United States Patent [19]

Habermeier

[11] 4,161,603
[45] Jul. 17, 1979

[54] DICARBOXYLIC ACIDS AND DICARBOXYLIC ACID ESTERS CONTAINING A BENZIMIDAZOLONE RADICAL

[75] Inventor: Jürgen Habermeier, Pfeffingen, Switzerland

[73] Assignee: Ciba-Geigy Corporation, Ardsley, N.Y.

[21] Appl. No.: 794,694

[22] Filed: May 6, 1977

[30] Foreign Application Priority Data

May 12, 1976 [CH] Switzerland ............... 5932/76

[51] Int. Cl.² ........................................... C07D 235/26
[52] U.S. Cl. ..................................... 548/305; 544/302; 544/314; 548/301; 548/307
[58] Field of Search ............... 260/260; 548/305, 307, 548/301

[56] References Cited
U.S. PATENT DOCUMENTS 3,954,790 5/1976 Habermeier ................... 548/305

Primary Examiner—Paul M. Coughlan, Jr.
Attorney, Agent, or Firm—Luther A. R. Hall

[57] ABSTRACT

Dicarboxylic acids or dicarboxylic acid esters, containing a N,N-heterocyclic radical, of the formula

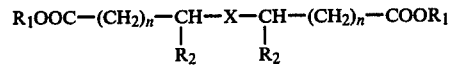

in which the two $R_1$ independently of one another each denote hydrogen, an alkyl with 1 to 4 C atoms or a phenyl, the two $R_2$ independently of one another each denote hydrogen or an alkyl with 1 to 10 C atoms, the two n represent identical or different numbers from 2 to 12 and X denotes a divalent monocyclic N,N-heterocyclic radical of benzimidazolone, parabanic acid, 2,2-dimethylimidazolidine-4,5-dione, 6-ethyluracil or barbituric acid are prepared by reacting 1 mol of the corresponding N,N-heterocyclic compounds with 2 mols of a compound of the formula

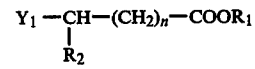

wherein $Y_1$ denotes a chlorine or bromine atom. The dicarboxylic acid compounds have a high stability to heat and therefore are very suited for the manufacture of polycondensates by the melt condensation process.

8 Claims, No Drawings

DICARBOXYLIC ACIDS AND DICARBOXYLIC ACID ESTERS CONTAINING A BENZIMIDAZOLONE RADICAL

The present invention relates to new aliphatic dicarboxylic acids and dicarboxylic acid esters containing a N,N-heterocyclic radical as well as processes for their manufacture.

Dicarboxylic acids which contain a N,N-heterocyclic radical in the molecule are already known. Thus, the manufacture of dicarboxylic acids containing hydantoin and alkylene-bis-hydantoins by cyanoethylation of hydantoin and alkylene-bis-hydantoins and subsequent hydrolysis of the resulting cyanoethyl compounds to give dicarboxylic acids is described in "Chemical Abstracts," Vol. 59, page 3,907(e). However, these dicarboxylic acids have the disadvantage that they do not have a high stability to heat and during hot further processing, for example during the manufacture of polyesters by the melt condensation process, easily redissociate into the hydantoin and acrylic compounds.

Furthermore, the manufacture of oligohydantoins and polyhydantoins containing carboxylic acid groups by reacting polyglycine esters with isocyanates containing carboxylic acid groups is described in German Offenlengungsschrift No. 1,906,492. This manufacturing process has the disadvantage, on the one hand, that the starting materials necessary for the process can only be obtained via expensive syntheses, and on the other hand the reaction of the polyglycine esters with the isocyanates, which proceeds with cyclisation, demands relatively high temperatures and the desired substances must be separated from products which have not been quantitatively cyclised and from the reaction mixture.

Furthermore, aliphatic dicarboxylic acids, containing a N,N-heterocyclic radical, with 1 or 2 C atoms in the alkylene chain and their dialkyl esters are known from German Offenlegungsschrift No. 2,453,326. These compounds also do not have a sufficiently high stability to heat and are thus ill-suited to hot further processing, for example by the melt condensation process.

It has now been found that new compounds which have a higher stability to heat and thus are better suited for the manufacture of polycondensates by the melt condensation process are obtained by reacting N,N-heterocyclic compounds with relatively long-chain aliphatic halogenocarboxylic acids or halogenocarboxylic acid alkyl esters.

The present invention thus relates to new dicarboxylic acids and dicarboxylic acid esters, containing a N,N-heterocyclic radical, of the formula I

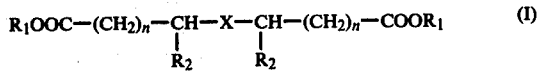

in which the two $R_1$ independently of one another each denote a hydrogen atom, an alkyl group with 1 to 4 C atoms or a phenyl group, the two $R_2$ independently of one another each denote a hydrogen atom or an alkyl group with 1 to 10 C atoms, the two n represent identical or different numbers from 2 to 12 and X denotes a N,N-heterocyclic radical of the formula

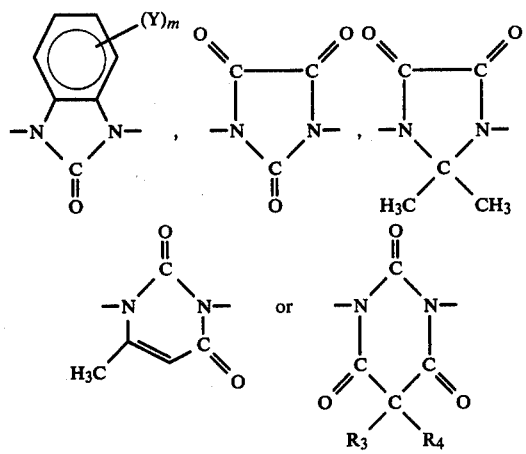

in which $R_3$ and $R_4$ each denote the methyl, ethyl or phenyl group, Y represents a bromine or chlorine atom and m equals zero or denotes a number from 1 to 4.

Preferably, in the formula I $R_1$ denotes an alkyl group with 1 to 4 C atoms or a phenyl group, $R_2$ denotes a hydrogen atom, n denotes a number from 2 to 4 and X denotes a N,N-heterocyclic radical of the formula

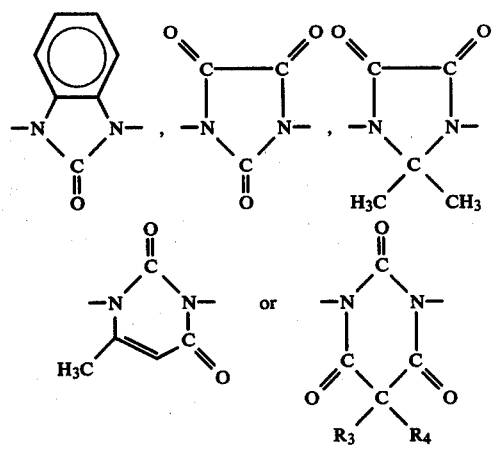

in which $R_3$ and $R_4$ each represent the methyl or ethyl group.

Those dicarboxylic acid diesters of the formula I in which $R_1$ denotes the methyl, ethyl or phenyl group, $R_2$ denotes a hydrogen atom, n denotes a number from 2 to 4 and X denotes the N,N-heterocyclic radical of the formula

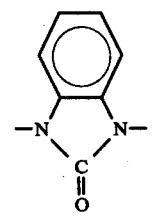

are particularly interesting.

The new dicarboxylic acids and dicarboxylic acid esters, containing a N,N-heterocyclic radical, of the formula I can be manufactured by reacting 1 mol of a N,N-heterocyclic compound of the formula IIa to IIe

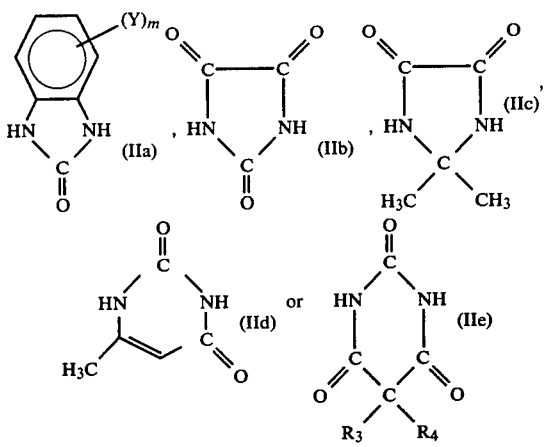

in which $R_3$, $R_4$, Y and m have the same meaning as in formula I, or their disodium or dipotassium salts, with 2 mols of a compound of the formula III

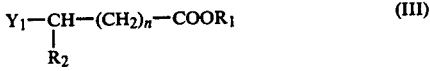

or mixtures of compounds of the formula III, in which $R_1$, $R_2$ and n have the same meaning as in formula I and $Y_1$ represents a chlorine or bromine atom, to give compounds of the formula I with the elimination of 2 mols of hydrogen chloride or bromide or sodium chloride or bromide or potassium chloride or bromide respectively.

Amongst the compounds of the formula IIe, methyl-substituted and/or ethyl-substituted barbituric acid are preferably employed. The compounds of the formulae IIb, IIc and IId are also compounds which are preferably used.

In a particularly preferred embodiment, unsubstituted benzimidazolone of the formula IIa is used as the N,N-heterocyclic compound.

The ω-chloro- or ω-bromo-carboxylic acid alkyl esters, especially the ω-chlorocarboxylic acid alkyl esters, or the ω-chlorocarboxylic acid or ω-bromocarboxylic acid phenyl esters of the formula III, that is to say compounds of the formula III in which $R_1$ denotes an alkyl group with 1 to 4 C atoms or a phenyl group, $R_2$ denotes a hydrogen atom, n denotes a number from 2 to 4 and $Y_1$ denotes a chlorine or bromine atom, especially a chlorine atom, are preferably used as the compound of the formula III.

In general, the conversion reaction is carried out in an organic solvent, the halogen-containing compounds of the formula III preferably being employed in a slight molar excess.

Solvents which can be used are, for example: dimethylformamide, dimethylacetamide, dimethylsulphoxide, N-methylpyrrolidone, tetramethylurea, benzene, toluene, xylene, chloroform and mixtures of these solvents.

It is also possible to carry out the conversion reaction without a solvent, that is to say in the melt. In this case, the reaction which proceeds with the elimination of a hydrogen halide is appropriately carried out in the presence of an acid acceptor which is added to the solvent in at least equivalent amounts, relative to the calculated amount of hydrogen halide liberated. Suitable acid acceptors for this are, in particular, potassium carbonate, sodium carbonate and calcium carbonate, sodium bicarbonate and also sterically hindered amines, such as N-methylaniline, dimethylaniline, diazabicyclooctane or also pyridine, furthermore, for example, also NaOH, KOH or tetramethylammonium hydroxide.

The conversion reactions are carried out in the temperature range from 20° to 200° C., preferably 50° to 150° C., the reaction temperatures to be chosen depending on the nature of the starting materials, on the composition of the solvent mixture and on the nature of the acid acceptors. In the preferred embodiment, the conversion reaction is carried out at temperatures rising from 60° to 130° C. or at constant temperatures between 75° C. and 130° C.

In a preferred embodiment of the process, the starting materials are employed in the theoretical molar ratio of 1:2, a mixture of dimethylformamide and benzene in a mixing ratio of 1:2 is used as the solvent and sodium carbonate or potassium carbonate is used as the acid acceptor. The water formed during the neutralisation reaction is continuously removed from the mixture azeotropically with benzene, toluene or xylene and separated off.

In order to isolate the reaction product, the reaction solution is filtered hot to remove the potassium halide formed, for example, when potassium carbonate is used as the acid acceptor and the desired product is obtained by allowing it to crystallise out of the reaction solution or by pouring the solution into water and precipitating the product or by concentrating the reaction solution to dryness and recrystallising the crude product in an organic solvent. Various organic solvents are suitable for this, such as, for example, methanol, acetone, ethanol or tetrahydrofurane.

If the N,N-heterocyclic compounds of the formulae II are used in the form of their disodium or dipotassium salts, these are initially rendered anhydrous by thorough drying and are then appropriately suspended in a polar, aprotic solvent, 2 to 2.2 mols of a compound of the formula III being employed per 1 mol of disodium or dipotassium salt. The reaction can be effected at temperatures between 20° and 180° C. Preferably, the conversion reaction is carried out in the temperature range from 60° to 130° C. Working up of the reaction solution is then carried out in a manner identical to that described above.

The dicarboxylic acids, containing a halogenated benzimidazolone radical, of the formula I can also be manufactured by halogenating dicarboxylic acids or dicarboxylic acid dialkyl esters, containing an unsubstituted benzimidazolone radical, of the formula I in a known manner with bromine or chlorine.

The N,N-heterocyclic compounds of the formulae IIa to IIe are known compounds, namely unsubstituted, chlorinated or brominated benzimidazolone (IIa), parabanic acid (IIb), 2,2-dimethylimidazolidine-4,5-dione (IIc), 6-methyluracil (IId) and unsubstituted barbituric acid or barbituric acid which is alkyl-substituted in the 5-position (IIe).

Chlorinated or brominated benzimidazolone is obtainable, for example, by the process described by H. Rochling in "Zeitschrift fur Naturforschung 256, page 954–960 (1970)" by reacting benzimidazolone with bromine or chlorine.

The halogenocarboxylic acids and halogenocarboxylic acid alkyl esters of the formula III are also known from the literature. ω-Halogenocarboxylic acids and their alkyl esters of the formula III in which R₂ represents a hydrogen atom are advantageously manufactured by the process described in "Houben-Weyl," Methoden der organischen Chemie (Methods of Organic Chemistry), Volume 5/3, page 828 (1962), by splitting suitable lactones with, for example, hydrogen chloride and, if appropriate, simultaneously esterifying the ω-chlorocarboxylic acid formed with the corresponding alcohol.

Halogenocarboxylic acids and their alkyl esters of the formula III in which R₂ represents an alkyl group or, if appropriate, a hydrogen atom can be manufactured by an addition reaction between HBr or HCl and mono-unsaturated aliphatic monocarboxylic acids and, if appropriate, subsequent esterification, the corresponding halogenocarboxylic acids or mixtures of isomeric halogenocarboxylic acids being formed, depending on the position of the double bond in the unsaturated monocarboxylic acid and the mechanism by which the addition reaction takes place (Markownikow rule). Thus, for example, a mixture of isomers consisting of 8-bromostearic acid and 9-bromostearic acid is obtained by an addition reaction between HBr and oleic acid or elaidic acid. Likewise, a mixture of isomers consisting of 12-bromobehenic acid and 13-bromobehenic acid is obtained by an addition reaction between HBr and erucic acid or brassidic acid.

The new dicarboxylic acid derivatives containing a N,N-heterocyclic radical are colourless, viscous liquids or crystalline substances which melt between 35° and 250° C. and are readily soluble in organic solvents, but are insoluble or only very slightly soluble in water.

The new dicarboxylic acid derivatives are valuable monomers which are suitable for the manufacture of plastics which are stable to heat. Thus, for example, the dicarboxylic acids and dicarboxylic acid diesters can be converted with diols into polyesters having very valuable mechanical properties. The diglycidyl esters obtained from the dicarboxylic acids by glycidylation with epihalogenohydrin can also be cured to give epoxide resins having valuable mechanical properties.

The dicarboxylic acids according to the invention are also suitable for modifying curable mixtures consisting of epoxide resins and carboxylic acid anhydrides.

EXAMPLE 1

1,3-Di-(3'-methoxycarbonyl-n-propyl)-benzimidazolone

A mixture of 26.8 g (0.2 mol) of benzimidazolone and 65.6 g (0.48 mol) of methyl γ-chlorobutyrate is stirred in a solvent mixture of 300 ml of benzene and 300 ml of dimethylformamide under the action of 30.4 g (0.22 mol) of dried potassium carbonate powder for 20 hours at 96°–101° C. The water formed during the reaction (by neutralisation of the hydrochloric acid, with potassium carbonate, formed during the condensation reaction) is continuously removed azeotropically from the mixture and separated off, whilst the benzene solution is recycled into the reaction vessel. After the reaction, the reaction mixture is filtered warm at 60°–80° C. and thus freed from potassium chloride and the residual potassium carbonate.

The filtrate is concentrated and the residue is dried at 90° C./0.2 mm Hg to constant weight.

64.5 g (96.4% of theory) of a viscous, clear liquid which has a pale light-brown colour are obtained.

Both the H-NMR spectrum (60 Mc; singlet at 7.1 ppm, triplet at 3.85–4.05 ppm, singlet at 3.65 ppm and multiplet at 1.9–2.5 and 2.8 ppm) and elementary analysis prove the structure of the new dicarboxylic acid ester.

Elementary analysis gives for C₁₇H₂₂N₂O₅:

| found: | calculated: |
|---|---|
| 61.20% C | 61.07% C |
| 6.60% H | 6.63% H |
| 8.80% N | 8.38% N |

For purification, the product can be distilled in a thin film evaporator, 260° C. being used at 0.1 mm Hg. The distillate is the desired product in the virtually colourless form:

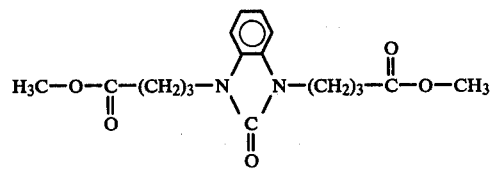

The crude product can also be purified by crystallisation and subsequent recrystallisation from ether. Completely colourless crystals which melt at 46°–48° C. are thus obtained.

Like the H-NMR spectrum, the micro-analysis shows that 1,3-di-(3'-methoxycarbonyl-n-propyl)-benzimidazolone is obtained as a very pure product.

Microanalysis for C₁₇H₂₂N₂O₅:

| found: | calculated: |
|---|---|
| 60.89% C | 61.07% C |
| 6.63% H | 6.63% H |
| 8.60% N | 8.38% N |

If a smaller amount of methyl chlorobutyrate is used and the reaction time is shortened, 1-(3-methoxycarbonyl-n-propyl)-benzimidazolone, which melts at 117.5°–119° C., can also be isolated as a by-product.

Microanalysis gives for C₁₂H₁₄N₂O₃:

| found: | calculated: |
|---|---|
| 61.42% C | 61.52% C |
| 5.91% H | 6.02% H |
| 12.27% N | 11.96% N |

The H-NMR spectrum also confirms the presence of this by-product thus obtained:

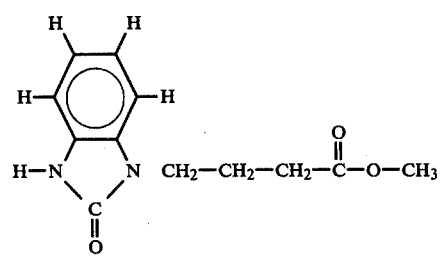

COMPARISON EXAMPLE 1,3-Di-(3'-methoxycarbonyl-n-propyl)-benzimidazolone according to Example 1 and 1,3-di-(2-ethoxycarbonyl-ethyl)benzimidazolone, described in German Offenlegungsschrift 2,453,326 and used as a comparison, which have identical molecular weights, are subjected to exposure to heat at 200° C. for several hours. The results obtained are compared in the Table which follows.

| Compound | according to German Offenlegungsschrift 2,453,326 | according to Example 1 |
|---|---|---|
| Structure | H₅C₂—O—C(=O)—CH₂—CH₂—N(ring)—CH₂—CH₂—C(=O)—O—C₂H₅ (benzimidazolidinone with 4 aromatic H) | H₃C—O—C(=O)—CH₂—CH₂—N(ring)—CH₂—CH₂—C(=O)—O—CH₃ (benzimidazolidinone with 4 aromatic H) |
| Empirical formula | C₁₇H₂₂N₂O₅ | C₁₇H₂₂N₂O₅ |
| Molecular weight | 334.16 | 334.16 |
| Decrease in weight by heat treatment at 200° C. | | |
| a) after 1.5 hours | 3.9% | 1.2% |
| b) after 3 hours | 6.1% | 2.0% |
| Stability to heat after 20 hours at 200° C.: comparison of the 4 aromatic protons to the number of protons in the aliphatic radical (H-NMR spectrum) | | |
| starting value: | 4/18 | 4/18 |
| final value: | 4/15.43 | 4/18 |

It can be seen from the Table that 1,3-di-(3'-methoxycarbonyl-n-propyl)-benzimidazolone according to the invention is not only less volatile but does not decompose chemically on exposure to heat (20 hours at 200° C.). On the other hand, according to H-NMR spectroscopic analysis the sample of 1,3-di-(2-ethoxycarbonylethyl)-benzimidazolone used as a comparison has been substantially decomposed with the splitting-off of

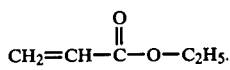

EXAMPLE 2

1,3-Di-(3'-methoxycarbonyl-n-propyl)-5,5-diethylbarbituric acid 18.4 g (0.1 mol) of 5,5-diethylbarbituric acid are reacted with 28.7 g (0.21 mol) of methyl γ-chlorobutyrate according to Example 1. 15.2 g (0.11 mol) of potassium carbonate powder are used as the acid acceptor and 100 ml of benzene and 100 ml of dimethylformamide are used as the solvent. The reaction is carried out exactly according to Example 1 and likewise worked up. In this manner, 38.3 g (99.7% of theory) of a clear, slightly discoloured viscous product are obtained.

Elementary analysis gives for $C_{18}H_{28}N_2O_7$:

| found: | calculated: |
| --- | --- |
| 56.20% C | 56.24% C |
| 7.40% H | 7.34% H |
| 7.40% N | 7.29% N |

The proton magnetic resonance spectrum (60 Mc; recorded in CDCl₃) also agrees with the structure below: triplet 0.6–0.95 ppm (6H); multiplet 1.8–2.5 ppm (12 H); singlet at 3.6 ppm (6H); triplet at 3.8–4.1 ppm (4H).

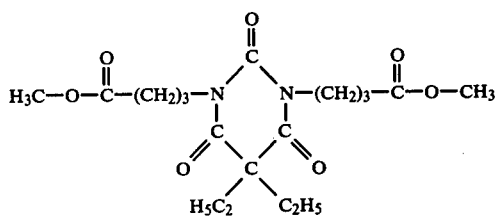

EXAMPLE 3

1,3-Di-(3'-methoxycarbonyl-n-propyl)-2,2-dimethylimidazolidine-4,5-dione 12.8 g (0.1 mol) of 2,2-dimethylimidazolidine-2,4-dione are reacted with 28.7 g (0.21 mol) of methyl γ-chlorobutyrate as described in Example 1 (solvent: 100 ml of benzene+100 ml of N,N-dimethylformamide); 15.2 g of dry potassium carbonate powder are used as the acid acceptor. After 12 hours, the mixture is worked up according to Example 1. 29.0 g (88.4% of theory) of a viscous, clear substance are obtained, which is recrystallised from 35 ml of methanol. Colourless crystals which melt at 111°–112° C. are isolated.

Elementary analysis gives for $C_{15}H_{24}N_2O_6$:

| found: | calculated: |
| --- | --- |
| 54.90% C | 54.87% C |
| 7.50% H | 7.37% H |
| 8.60% N | 8.53% N |

The H-NMR spectrum shows, by the singlet at 1.6 ppm (2×CH₃), the multiplet at 1.8–2.6 ppm

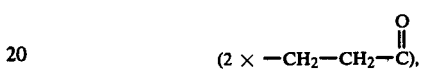

the triplet at 3.3–3.6 ppm (2×—N-CH₂—) and the singlet at 3.7 ppm (2×H₃C-O), that the structure below is correct for the new diester:

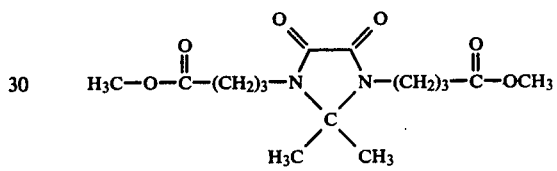

EXAMPLE 4

1,3-Di-(3'-methoxycarbonyl-n-propyl)-4,5,6,7-tetrabromobenzimidazolone 45.48 g (0.1 mol) of 4,5,6,7-tetrabromobenzimidazolone are suspended in 250 ml of dimethylformamide and 75 ml of toluene and 27.4 g (0.2 mol) of finely powdered, dry potassium carbonate are added. 30.07 g (0.22 mol) of methyl γ-chlorobutyrate are added to this suspension and the mixture is heated up to the reflux temperature (internal temperature 108°–120° C.), whilst stirring. The toluene serves to remove water azeotropically. After 25 hours, the mixture is cooled to 80°–85° C. and filtered whilst still hot. The solution is concentrated to dryness and the desired product is isolated in the form of colourless crystals. Yield: 58.35 g (89.1% of theory).

Elementary analysis for $C_{17}H_{18}Br_4N_2O_5$

| found: | calculated: |
| --- | --- |
| 31.30% C | 31.42% C |
| 2.84% H | 2.79% H |
| 4.41% N | 4.31% N |
| 48.92% Br | 49.16% Br |

The product melts at 128.5°–130° C. The H-NMR spectrum and microanalysis agree with the following structural formula:

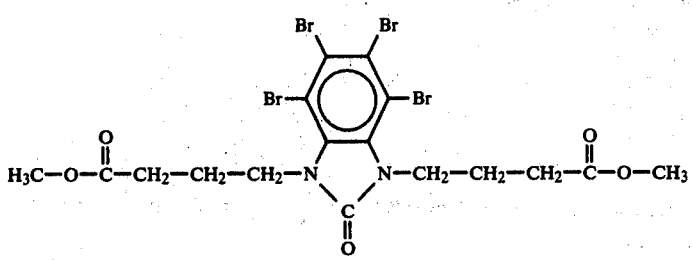

EXAMPLE 5

1,3-Di-(10'-methoxycarbonyl-n-decyl)-benzimidazolone

A mixture of 67 g (0.5 mol) of benzimidazolone, 76 g (0.55 mol) of potassium carbonate and 279.6 g (1.0 mol) of methyl 11-bromoundecanoate are heated to 95°–98° C. (bath temperature 130°–140° C.) in a mixture of 500 ml of dimethylformamide and 350 ml of benzene, whilst stirring well. The water formed during the reaction is continuously removed azeotropically. The condensation reaction has ended after 5 hours. The reaction mixture is filtered whilst still warm and then completely concentrated. In this manner, the crude product is obtained in quantitative yield in the form of an ochre-coloured, thick crystal sludge. The procedure for purification can be as follows:

Because they are sparingly soluble, the starting materials and monosubstituted benzimidazolone can be separated off by treatment with ether/hexane. The filtrate is concentrated and 174.1 g (65.6% of theory) of the desired product are obtained as a yellowish oil which slowly crystallises and which can be recrystallised from hexane. A light ochre-coloured crystal powder which melts at 35°–36° C. is obtained.

The H-NMR spectrum (60 Mc) agrees with the following structure:

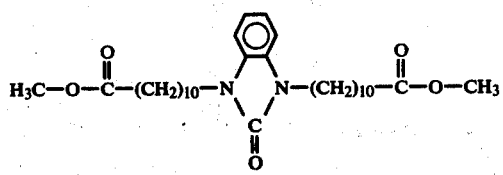

EXAMPLE 6

1,3-Di-(3'-butoxycarbonyl-n-propyl)-parabanic acid 23.8 g (0.2 mol) of crude parabanic acid, 85.9 g (0.48 mol) of butyl 4-chlorobutyrate and 30.4 g (0.22 mol) of dry potassium carbonate powder are heated to 100° C. in a mixture of 250 ml of dimethylformamide and 200 ml of benzene in the course of 5 hours, whilst stirring. The water formed during the reaction is removed azeotropically. The mixture is then kept for a further 5 hours under these conditions, the salt residue is subsequently filtered off and the filtrate is concentrated. 20.4 g of residue are obtained which is purified by adding ether and filtering off the suspended matter. The ethereal solution is concentrated to dryness and the residue is then dried at 140° C./0.1 mm Hg to constant weight. 8.9 g of the desired product are thus obtained in the form of a clear, highly viscous oil.

Elementary analysis gives for $C_{19}H_{30}N_2O_7$:

| found: | calculated: |
|---|---|
| 57.09% C | 57.27% C |
| 7.40% H | 7.59% H |
| 7.19% N | 7.03% N |

The H-NMR spectrum agrees with the following structure:

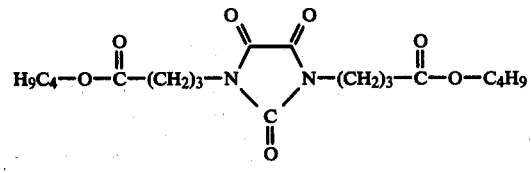

EXAMPLE 7

1,3-Di-(5'-methoxycarbonyl-n-pentyl)-benzimidazolone 13.4 g (0.1 mol) of benzimidazolone are reacted with 50.2 g (0.24 mol) of methyl 6-bromohexanoate in a solvent mixture of 100 ml of dimethylformamide and 100 ml of benzene, 15.2 g of dry potassium carbonate powder being used as the acid acceptor. The reaction is carried out at 98°–99° C., whilst stirring well, the water formed during the reaction being removed azeotropically. Thereafter, the hot reaction mixture is filtered and the filtrate is concentrated to dryness. A yellowish oil (39.0 g), which completely crystallises on standing, is obtained in quantitative yield. The purification can be carried out in the customary manner. The product thus prepared shows a proton magnetic resonance spectrum which agrees with the following structure:

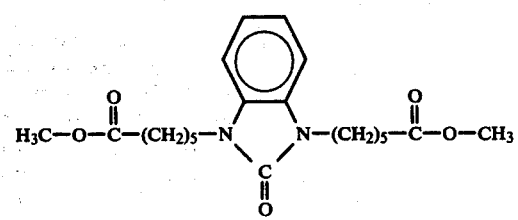

EXAMPLE 8

1,3-Di-(3'-methoxycarbonyl-n-propyl)-parabanic acid 11.9 g (0.1 mol) of parabanic acid (imidazolidine-2,4,5-trione) are stirred with 32.8 g (0.24 mol) of methyl γ-chlorobutyrate, with the aid of 15.2 g (0.11 mol) of dry potassium carbonate powder, in 250 ml of dimethylformamide/benzene (1:1) at 100° C. for 8 hours. The benzene is then distilled off and the mixture is stirred for a further 2 hours at 140° C. The mixture is filtered hot, the filtrate is concentrated to dryness and 31.3 g of the desired crude product (99.7% of theory) are obtained. 30 ml of ether and 12 ml of acetone are added to the crude product, the mixture is clarified by filtration, the filtrate is evaporated to dryness and the residue is dried to constant weight at 115° C. under 0.3 mm Hg. 31.2 g (99.4%) of a clear, yellow, viscous liquid are obtained.

Combustion analysis gives for $C_{13}H_{18}N_2O_7$:

| found: | calculated: |
|---|---|
| 49.85% C | 49.68% C |
| 5.86% H | 5.78% H |
| 9.02% N | 8.92% N |

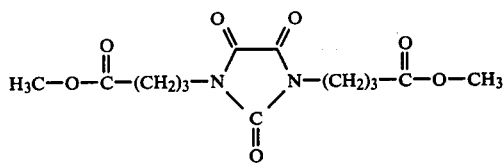

EXAMPLE 9

1,3-Di-(3'-ethoxycarbonyl-n-propyl)-4,5,6,7-tetrabromobenzimidazol-2-one 9.0 g (0.02 mol) of 4,5,6,7-tetrabromobenzimidazol-2-one (melting point >300° C.) are mixed with 6.3 g (0.042 mol) of ethyl 4-chlorobutyrate and 3.0 g (0.022 mol) of dried potassium carbonate powder at room temperature. After adding 50 ml of a solvent mixture of dimethylformamide/benzene (3:2), the reaction mixture is heated to 98°–100° C. During this procedure, an azeotropic circulatory distillation starts, by which the water formed during the reaction is removed from the mixture. After a total of 8 hours, the mixture is cooled to room temperature, filtered and the filtrate concentrated to dryness. An ochre-coloured solid substance is obtained in quantitative crude yield (13.6 g). For purification, the product is recrystallised from 320 ml of methanol. In this manner, 6.7 g of colourless, scaly crystals (49.3% of theory) are obtained which melt at 118°–118.6° C. A further amount of the product can be obtained from the mother liquor.

Elementary analysis gives for $C_{19}H_{22}Br_4N_2O_5$:

| found: | calculated: |
|---|---|
| 34.03% C | 33.66% C |
| 3.30% H | 3.27% H |
| 4.30% N | 4.13% N |
| 47.40% Br | 47.14% Br |

The 60 Mc H-NMR spectrum agrees with the following structure:

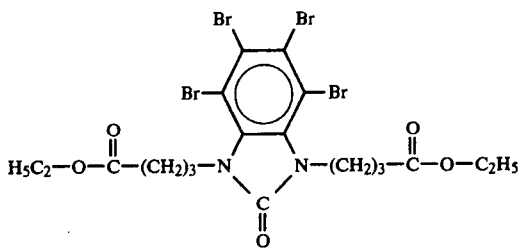

EXAMPLE 10

1,3-Di-(3'-phenoxycarbonyl-n-propyl)-5-ethyl-5-phenylbarbituric acid

A mixture of 77.1 g (0.25 mol) of dipotassium phenylethylbarbiturate and 104.5 g (0.525 mol) of phenyl chlorobutyrate in 500 ml of dimethylformamide is heated to 122°–125° C., whilst stirring. The reaction mixture is kept under these conditions for 5 hours and then filtered whilst still hot.

After concentrating the mixture to dryness, the desired crude product is obtained in 80.4% yield (112 g). In order to separate off unreacted residues of the starting materials, the crude product is stirred in 200 ml of ether, the mixture is allowed to stand overnight, the suspended matter is filtered off, and the filtrate is concentrated to dryness. The residue is then subjected to treatment at 150° C. (0.2 mm Hg) to constant weight. The resulting, purified, clear amorphous material is obtained in 56.7% yield. The analysis for $C_{32}H_{32}N_2O_7$ and the H-NMR spectrum (60 Mc) agree with the following structure:

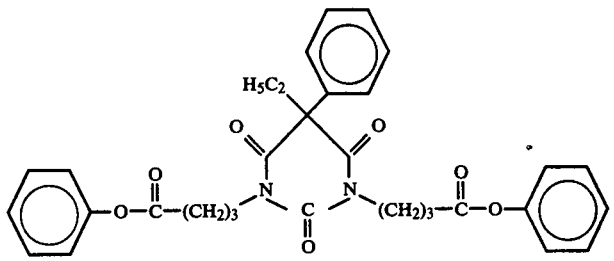

EXAMPLE 11

1,3-Di-(3'-methoxycarbonyl-n-propyl)-6-methyluracil 40.4 g (0.2 mol) of the dipotassium salt of 6-methyluracil and 57.4 g (0.42 mol) of methyl 4-chlorobutyrate are stirred in 350 ml of dimethylformamide for 10 hours at 125° C. The mixture is filtered and the clear solution is concentrated to dryness, 48.2 g of the desired crude product being obtained as a yellowish semi-solid mass (73.8% of theory).

In order to separate off small residues of unreacted starting material, 100 ml of methanol are added to the crude product and the insoluble constituent is filtered off. After concentrating, this operation is repeated again with 80 ml of ether. The product is then dried under a high vacuum (0.2 mm Hg) at 120° C. to constant weight. A yellowish resin-like viscous product is obtained. The H-NMR spectrum shows that the product essentially consists of the substance having the following formula:

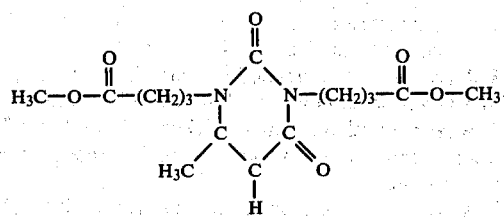

APPLICATION EXAMPLES

EXAMPLE I

Copolyester based on poly(butylene terephthalate) and 25 mol % of 1,3-di-(3'-methoxycarbonyl-n-propyl)-5,5-diethylbarbituric acid A mixture of 29.13 g (0.15 mol) of dimethyl terephthalate, 19.22 g (0.05 mol) of 1,3-di-(3'-methoxycarbonyl-n-propyl)-5,5-diethylbarbituric acid and 30.1 g (1.0 mol) of 1,4-butanediol is subjected to a transesterification reaction and polycondensation reaction under the catalytic action of 2.4 ml of a 0.02 molar solution of tetraisopropyl orthotitanate in n-butanol according to the following conditions.

1 hour: 140°–180° C./normal pressure/$N_2$ atmosphere
1 hour: 180°–220° C./normal pressure/$N_2$ atmosphere
1 hour: 220°–240° C./normal pressure/$N_2$ atmosphere
45 minutes: 240°–285° C./200 mm Hg→15 mm Hg/$N_2$ atmosphere
25 minutes: 285° C./0.2–0.3 mm Hg/$N_2$ atmosphere The polycondensate is poured out on a metal sheet, under $N_2$, in order to cool it. The copolyester thus obtained is partially crystalline, virtually colourless (pale greyish tinge) and has a relative viscosity of 1.66.

EXAMPLE II

Copolyester based on poly(butylene terephthalate) and 25 mol % of 1,3-di-(3'-methoxycarbonyl-n-propyl)-2,2-dimethylimidazolidine-4,5-dione A mixture of 11.65 g (0.06 mol) of dimethyl terephthalate, 6.57 g (0.02 mol) of 1,3-di-(3'-carbomethoxy-n-propyl)-2,2-dimethylimidazolidine-4,5-dione and 36.04 g (0.4 mol) of 1,4-butanediol is subjected to a transesterification reaction and polycondensation reaction under the catalytic action of 0.9 ml of a 0.02 molar solution of tetraisopropyl orthotitanate in n-butanol according to the conditions of Example I. A partially crystalline, slightly discoloured copolyester is isolated, the relative viscosity of which is 1.33.

EXAMPLE III

Copolyester based on poly(butylene terephthalate) and 25 mol % of 1,3-di-(3'-methoxycarbonyl-n-propyl)-benzimidazolone The mixture which follows is subjected to a transesterification reaction and polycondensation reaction according to Example I, 2.4 ml of a 0.02 molar solution of tetraisopropyl orthotitanate in n-butanol serving as the catalyst: 29.13 g (0.15 mol) of dimethyl terephthalate, 16.72 g (0.05 mol) of 1,3-di-(3'-methoxycarbonyl-n-propyl)-benzimidazolone and 90.1 g (1.0 mol) of 1,4-butanediol.

A virtually colourless copolyester which is partially crystalline and has a relative viscosity of 1.30 is obtained.

EXAMPLE IV 1,3-Bis-(3'-carboxy-n-propyl)-4,5,6,7-tetrabromobenzimidazolone from 1,3-bis-(3'-methoxycarbonyl-n-propyl)-benzimidazolone 70.0 g (0.209 mol) of the 1,3-bis-(3'-methoxycarbonyl-n-propyl)-benzimidazolone prepared according to Example 1 are suspended in a mixture of 2.5 liters of water and 50 ml of dioxane and heated to 92°–95° C., whilst stirring. A white emulsion is thus formed. 200 g (1.26 mols) of bromine are added dropwise to this emulsion in the course of 3 hours and the mixture is stirred vigorously at a reaction temperature of 90°–95° C. At the start, the bromine is taken up very rapidly so that 60% of the amount of bromine are added in the course of the first hour of the dropwise addition; thereafter, the bromine is metered in correspondingly more slowly.

After the dropwise addition, the aqueous solution is coloured light brown by the excess of bromine. A precipitate forms which gradually becomes crystalline during further stirring at 90° C. The mixture is stirred for a further 5 hours at 90° C. and cooled to room temperature and the crystals are isolated by filtration.

After drying, 123 g of colourless crystals (94.6% of theory) which melt at 211° to 215° C. are obtained.

This crude product can be recrystallised from 1.5 liters of dioxane/$H_2O$ (1:1).

The pure product thus obtained melts at 236.5°–238.2° C. Its structure is confirmed by the absence of the signals for aromatic protons in the 60 Mc H-NMR spectrum and by the presence of the signals for the N-$CH_2$-$CH_2$-$CH_2$-COOH grouping.

Microanalysis gives for $C_{15}H_{14}Br_4N_2O_5$:

| found: | calculated: |
| --- | --- |
| 28.84% C | 28.97% C |
| 2.27% H | 2.27% H |
| 4.54% N | 4.50% N |
| 51.55% Br | 51.39% Br |

The resulting tetrabromo compound thus corresponds to the formula:

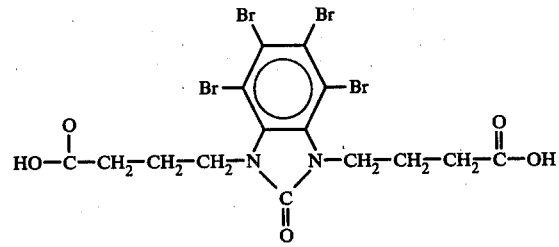

What is claimed is:
1. A benzimidazolone compound of the formula

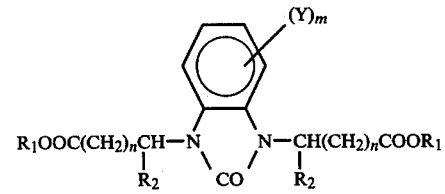

in which the two $R_1$ independently of one another each denote hydrogen, alkyl of 1 to 4 carbon atoms or phenyl, the two $R_2$ independently of one another each denote hydrogen or alkyl with 1 to 10 carbon atoms, the two n represent identical or different numbers from 2 to 12, Y represents bromo or chloro, and m equals zero or denotes a number from 1 to 4.

2. A compound according to claim 1 wherein $R_1$ denotes alkyl of 1 to 4 carbon atoms or phenyl, $R_2$ is hydrogen, n denotes a number from 2 to 4, and m is zero.

3. A compound according to claim 2 wherein $R_1$ is methyl, ethyl or phenyl.

4. A compound as claimed in claim 1, which is 1,3-di-(3'-methoxycarbonyl-n-propyl)-benzimidazolone.

5. A compound as claimed in claim 1, which is 1,3-di-(10'-methoxycarbonyl-n-decyl)-benzimidazolone.

6. A compound as claimed in claim 1, which is 1,3-di-(5'-methoxycarbonyl-n-pentyl)-benzimidazolone.

7. A compound as claimed in claim 1, which is 1,3-di-(3'-methoxycarbonyl-n-propyl)-4,5,6,7-tetrabromobenzimidazolone.

8. A compound as claimed in claim 1, which is 1,3-di-(3'-ethoxycarbonyl-n-propyl)-4,5,6,7-tetrabromobenzimidazolone.

* * * * *